(12) United States Patent
Shinmyo et al.

(10) Patent No.: US 6,229,070 B1
(45) Date of Patent: May 8, 2001

(54) METHOD OF STABLE GENE EXPRESSION IN A TRANSGENIC PLANT UTILIZING AN INSULATOR NUCLEOTIDE SEQUENCE FROM THE SEA URCHIN ARYLSULFATASE GENE

(75) Inventors: Atsuhiko Shinmyo, Ikoma-gun; Kazuya Yoshida; Ko Kato, both of Ikoma; Koji Akasaka, Higashihiroshima; Takaaki Kusumi, Suita; Yoshikazu Tanaka, Ohtsu, all of (JP)

(73) Assignee: Nara Institute of Science and Technology (JP)

( * ) Notice: Subject to any disclaimer, the term of this patent is extended or adjusted under 35 U.S.C. 154(b) by 0 days.

(21) Appl. No.: 09/444,570

(22) Filed: Nov. 19, 1999

(30) Foreign Application Priority Data

Dec. 9, 1998 (JP) .................................................. 10-349625
Sep. 7, 1999 (JP) .................................................. 11-253174

(51) Int. Cl.⁷ .............................. A01H 5/00; C12N 15/82
(52) U.S. Cl. ............................................ 800/298; 800/278
(58) Field of Search ..................................... 435/440, 462, 435/468, 469; 800/278, 279, 280, 288, 294, 298

(56) References Cited

U.S. PATENT DOCUMENTS 5,834,269 * 11/1998 Yasue et al. ....................... 435/172.3
6,037,525 * 8/1996 Thompson et al. ................... 800/298

* cited by examiner

*Primary Examiner*—Amy J. Nelson
*Assistant Examiner*—David Kruse
(74) *Attorney, Agent, or Firm*—Burns, Doane, Swecker, & Mathis, L.L.P.

(57) ABSTRACT

A method for the stable expression of an introduced exogenous gene in a plant or plant cell is provided. Stable expression of an exogenous gene that was introduced was achieved by operably linking an upstream sequence of sea urchin arylsulfatase gene as an insulator.

10 Claims, 7 Drawing Sheets

A    p35S core-GUS

B    INS(+)-p35S core-GUS

C    INS(-)-p35S core-GUS

D    INS-p35S core-GUS-INS

E    p35S core-GUS-INS

F    500-p35S core-GUS

Clones derived from transformed BY2 cells 1  2  3  4  5  6  7  8  9  10 11

METHOD OF STABLE GENE EXPRESSION IN A TRANSGENIC PLANT UTILIZING AN INSULATOR NUCLEOTIDE SEQUENCE FROM THE SEA URCHIN ARYLSULFATASE GENE

BACKGROUND OF THE INVENTION

1. Field of the Invention

This invention relates to a method of gene transfer, which enables stable expression of an exogenous gene in a plant cell.

2. Description of Related Art

Many kinds of transgenic plants with an exogenous gene introduced have been produced to render various characteristic to a plant. In the production of transgenic plants, the diversity of gene expression is observed among individual transgenic plants. It is considered that the diversity is caused by the position of introduced gene in a chromosome. When an exogenous gene is introduced into active chromatin region, high expression of the exogenous gene would be obtained. On the contrary, when an exogenous gene is introduced into inert chromatin region, sufficient expression of the gene would not be obtained (Galli, Current opinion in plant technology (1998) 1:166–172, Matzke et al., Current opinion in plant technology (1998) 1:142–148). Such effect described above is called "position effect". Because of the position effect, a transgene, which is introduced into a plant, exhibits absolute failure of expression, only weak expression or suspension of expression caused by plant growth or exogenous environment. This phenomenon serves as a barrier to commercialization of a transgenic plant and establishment of a method to stabilize expression of an introduced gene have been demanded.

Recently, some transformants, wherein genes of various kinds are introduced, revealed constant expression of the gene independent of its introduced position in the chromosome. The factors concerning such phenomenon are classified into three cases. These are, insulator, LCR (locus control region) and MAR (matrix attachment region) and involvement of such factors on constant expression is suggested. These three factors function as boundaries in a chromosome and blockade effects of near-existing chromatin, though the mechanism of action of these factors differs from each other.

When an insulator is located between an enhancer and a promoter, the insulator operates to blockade the effect of the enhancer as a silencer. In a higher eukaryotic plant, an enhancer and a silencer might cause an effect on transcriptional activity of not only a certain promoter, but also plural promoters. Therefore, plural elements might cause effects randomly in a chromosome. This phenomenon might work to render diversity on gene expression. On the other hand, a mechanism to restrict the enhancer function or the silencer function might be necessary for precise regulation of gene expression. At present, it is speculated that, an insulator might operate to restrict these functions.

LCR is a region higher-sensitive to DNaseI. LCR might form active chromatin, which facilitates physical accession of promoter and various transcriptional factors.

MAR contains an adenine, thymine (AT) rich sequence and a topoisomerase II recognition sequence. Moreover, MAR exhibits nuclear-membrane binding activity under in virto condition. MAR is considered to exist more than every 10–100 kb in a chromosome, and the chromosome binds to nuclear membrane through these regions to form conformation of the chromosome. MAR is indispensable for compaction of chromosome in a limited space of nucleus. The knowledge indicating that the MAR might be involved in the regulation of gene expression is accumulating in recent researches. For example, the analysis of MAR derived from kappa light chain immunogloblin gene of mouse revealed following knowledge.

(1) MAR is necessary for gene expression in the process of development.

(2) Inactivation of gene expression is caused by deletion of MAR through high-order methylation of DNA.

Moreover, a transcriptional unit of one or more gene is contained in a chromatin roop formed among plural MAR's. The analysis of beta globin gene wherein a cluster is formed in the loop revealed that, mutual affinity of each gene was indispensable for appropriate regulation and function of the gene. From these knowledge, it is speculated that, one chromatin loop among MAR's might form an independent unit, and gene expression might be regulated per the unit.

As described above, stable expression of introduced gene is demanded to obtain a practical transformant, regardless of whether the transformant is an animal or a plant. As described heretofore, avoidance of effect caused by surroundings of introduced location, a position effect, is indispensable. Therefore, the possibility that the position effect might be avoided by insertion of LCR, MAR or insulator have been investigated. In animal cell, LCR and insulator functioned as expected and the diversity of gene expression among transformants decreased (Akasaka, Cell Engineering (1997)16:1476–1484, Yasue et al. JP 6550/97). Concerning MAR, investigations performed by a promoter gene or a reporter gene did not exhibit consistent results. Therefore, stable expression of introduced gene was not achieved in many cases. In plants, this result might be caused by following phenomenon.

(1) Plenty of MAR's might operate to increase expression of introduced gene.

(2) When plural copies are introduced, expression of introduced gene might be suppressed by other effects than position effect, for example, specific methylation of DNA.

Therefore, MAR might not function as a boundary on the chromosome necessarily (Galli, Current opinion in plant technology (1998)1:166–172, Matzke et al., Current opinion in plant technology (1998)1:142–148), resulting in failure of generalization of the technique using MAR.

SUMMARY OF THE INVENTION

Therefore, the inventors paid attention to an insulator, which blockades the function of an enhancer and a silencer. There is no prior investigation concerning the effect of an insulator on the expression of a transgene in a plant. Then availability of insulator in a plant remained to be unknown. In this invention, an insulator was adopted to decrease the position effect of a transgene in a plant. Expression of an introduced gene was stabilized in a cultured tobacco cell, without increase of the expression of the gene. This invention provides a method for stable expression of a transgene in a plant.

Hitherto, insulators have been identified from various organisms, for example, Drosophila. The examples of insulators identified are, gypsy insulator, scs-scs' insulator and Fab-7 insulator originated from Drosophila, beta globin insulator originated from chicken, apoB insulator originated from chicken and human. The identification of proteins involved in insulator function have been performed recently, in particular, the analysis on gypsy insulator, scs-scs' insulator is advanced.

This invention provides a method for stable expression of an exogenous gene in a plant cell or in a plant body. It was achieved by concurrent introduction of an exogenous gene and an insulator derived from an organism of heterogeneous species against said plant. Moreover, this invention provides a transgenic plant comprising a plant having an exogenous gene and an insulator. Specifically, the insulator derived from sea urchin arylsulfatase gene was adopted in this invention.

Theoretically, any plant can be adopted as a host plant to be introduced an exogenous gene. The examples of plants preferred to be adopted as a host plant are as described below. These are useful cultivated plants such as tobacco, Arabidopses or petunia, crops such as rice, maize, potato, sweet potato, soybean, strawberry or eggplant and trees such as blue gum or white poplar.

Moreover, any gene can be adopted as an exogenous gene to be introduced in a host plant. The examples of exogenous genes preferred to be introduced in a host plant are as described below. These are disease or insect injury resistance genes such as peroxidase gene or chitinase gene, genes for ectoine biosynthesis such as L-2,4-diaminobutyric acid acetyltransgerase, L-2,4-diaminobutyric acid transaminase and ectoine synthetase, genes for betaine biosynthesis such as choline oxidase and second metabolite producing gene such as fatty acid biosynthesis. The plants and genes described above are intended to be preferred examples, not to be intended to limit the range of this invention.

These and other features and advantages of this invention will become apparent upon a reading of the detailed description and drawings.

DETAILED DESCRIPTION OF EMBODIMENTS (Production of a Binary Vector Containing an Insulator)

In this experiment, upstream sequence (from −2686 to −2109) derived from sea urchin arylsulfatase (Ars) gene was used as an insulator. This sequence is described in Akasaka et al. Dev. Growth & Differ. (1994) 36:633–636. As a model promoter, a core promoter of cauliflower mozaic virus (CaMV) 35S promoter (90 bp) was used. Introduction of GUS fusion gene of conventional CaMV 35S core promoter into the chromosome of BY2 cell results in inactivation of the gene expression in high frequency. The existence of an intracellular threshold on the extent of mRNA accumulation and a mechanism for specific degradation of mRNA accumulated beyond the threshold have been reported. In addition to the position effect, the mRNA accumulation mechanism described above might be involved in the inactivation. The insulator alleviates the position effect by functioning as a boundary on a chromosome. But gene silencing caused by threshold of mRNA accumulation might not be alleviated by the insulator. Therefore, the CaMV 35S core promoter, which exhibits activity lower than intracellular threshold, was used in this experiment.

Figure 1:
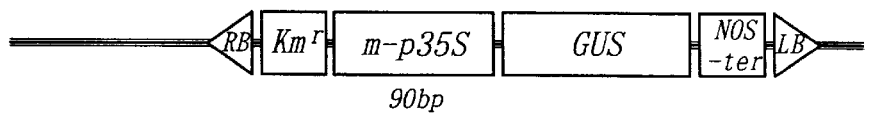
FIGS. 1A–1F are schematic views showing structure of T-DNA of binary plasmids introduced into cultured tobacco cell.
Figure 1:
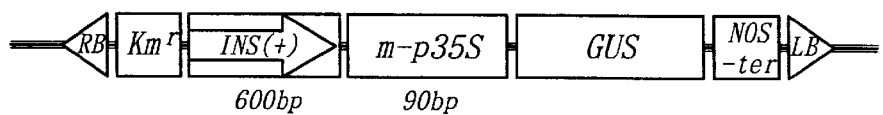
Figure 1:
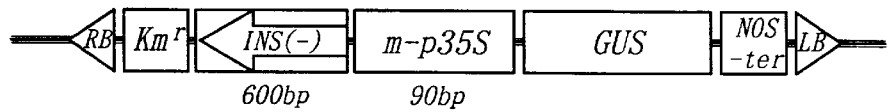
Figure 1:
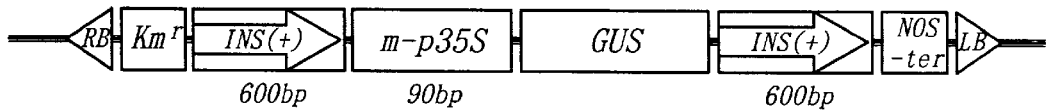
Figure 1:
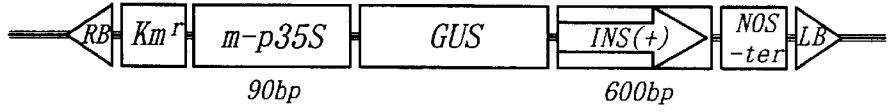
Figure 1:
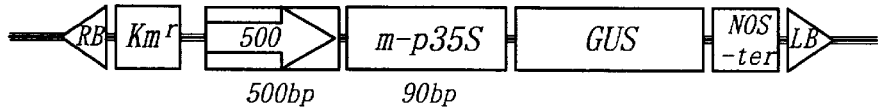

A genomic DNA to be introduced in a plant cell was ligated to binary vector pBI101 throughly. In the DNA region (T-DNA), which exists between two border sequences of the binary vector, a gene responsible for kanamycin resistance was introduced previously. The binary plasmids constructed are listed below and schematic views of T-DNA region of each plasmid are shown in FIG. 1.
(A) p35Score-GUS: The GUS gene is ligated to downstream of (CaMV)35S core promoter.
(B) INS(+)-p35Score-GUS: An insulator sequence (from −2686 to −109) of sea urchin arylsulfatase (Ars) gene is ligated to 5'-upstream of p35Score-GUS in sense direction.
(C) INS(−)-p35Score-GUS: Said insulator sequence is ligated to 5'-upstream of p35Score-GUS in anti-sense direction.
(D) INS-p35Score-GUS-INS: Said insulator sequence is ligated to both 5'-upstream and 3'-downstream of p35Score-GUS in sense direction (The GUS gene is located between two insulators described above).
(E) p35Score-GUS-INS: Said insulator sequence is ligated to 3'-downstream of p35Score-GUS in sense direction.
(F) 500-p35Score-GUS: Five hundred bp of HindIII digested DNA fragment derived from lambda phage genomic DNA is ligated to 5'-upstream of p35Score-GUS (used as negative control).

(Introduction into Cultured Tobacco Cell)

Each binary plasmid (A–F described above) was introduced into chromosome of cultured tobacco cell (BY2), using Agrobacterium infection method as described by Gynheung et al. (Gynheung et al., Plant Physiol. (1985) 79:568–570). The putative transformed cell, wherein the target gene was assumed to be introduced, was selected by phenotype of kanamycin resistance.

After subculture of BY2 for 7 days, the BY2 cell was transplanted to modified LS medium. The day of transplantation was considered to be the 0th day. The Agrobacterium bearing the target gene was inoculated to LB medium at the second day and cultured under shaking at 28° C. for 2 days in the dark. The BY2 cell and the Agrobacterium were put on a dish at the 4th day, mixed by gentle shaking, sealed by para-film and co-cultured at 25° C. for two days in the dark. The co-cultured medium was recovered at the 6th day, centrifuged at 700 rpm for 3 min and the supernatant containing the Agrobacterium was removed. The BY2 cell was centrifuged 3 to 5 times in modified LS medium to wash the BY2 cell. After washing, the agrobacterium was diluted appropriately by modified LS medium and inoculated into LS medium containing kanamycin and carbenicillin. The inoculated medium was sealed by para-film and cultured at 25° C. in the dark. Two or three weeks later (about one month later from beginning of the experiment), the callus cell was transplanted to fresh modified LS plate. Putative transformant was selected by three or four weeks of cultivation at 25° C. in the dark. Three or four weeks later (about two months later from beginning of the experiment), the proliferated cell which formed half moon like callus was transplanted to modified LS medium containing kanamycin and carbenicillin and cultured at 25° C. in the dark. Two or three weeks later (two and half months later from beginning of the experiment), the BY-2 cell was taken and transplanted to modified LS medium containing kanamycin and carbenicillin.

(Measurement of Beta-Glucuronidase Activity)

Fifty clones of transformants were obtained independently for each gene and beta-glucuronidase activity (GUS activity) was measured for each clone.

One ml of cultured cell suspension was sampled, centrifuged at 1000 rpm for 3 min at 4° C. and the supernatant was discarded. Five hundreds $\mu$l of GUS lysis buffer (50 mM $NaH_2PO_4/Na_2HPO_4$ pH7.0, 10 mM EDTA, 0.1% Triton X-100, 0.1% sarcosine, 10 mM 2-mercaptoethanol) was added to the pellet and homogenized on ice. It was centrifuged at 15000 rpm for 5 min at 4° C. and the supernatant (crude enzyme solution) was sampled. One mM of 4-methyl-umbelliferyl-$\beta$-D-glucronide (4MUG) was added to 100 $\mu$g of crude enzyme solution and incubated for 30 min at 37° C. Three ml of stop solution (0.2M $Na_2CO_3$) was added and fluorescence was measured by fluorometer.

The fluorescence patterns observed at GUS activity measurement were shown in FIGS. 2 to 7 and results of GUS activity quantified from these patterns were summarized in Table 1.

The extent of GUS activity was indicated by following marks in Table 1.

TABLE 1

GUS activity expression pattern of
transformed BY2 cells with each fusion gene introduced

| Introduced gene | +++ | ++ | + | − | total |
|---|---|---|---|---|---|
| p35Score-GUS | 12 | 17 | 7 | 14 | 50 |
| INS(+)-p35Score-GUS | 26 | 24 | 0 | 0 | 50 |
| INS-p35Score-GUS-INS | 37 | 12 | 1 | 0 | 50 |
| p35Score-GUS-INS | 18 | 16 | 6 | 10 | 50 |
| 500-p35Score-GUS | 5 | 12 | 3 | 30 | 50 |

(Stabilization of Expression of Introduced Gene by Ars Insulator)

Figure 2:
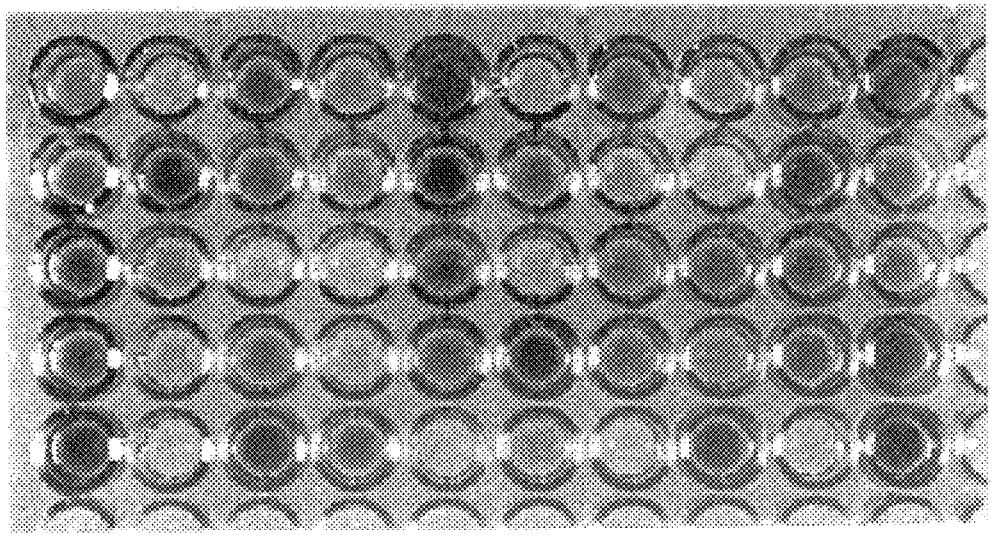
FIG. 2 is a photograph showing GUS activity staining of BY2 cell (50 samples) with p35Score-GUS introduced.
Figure 3:
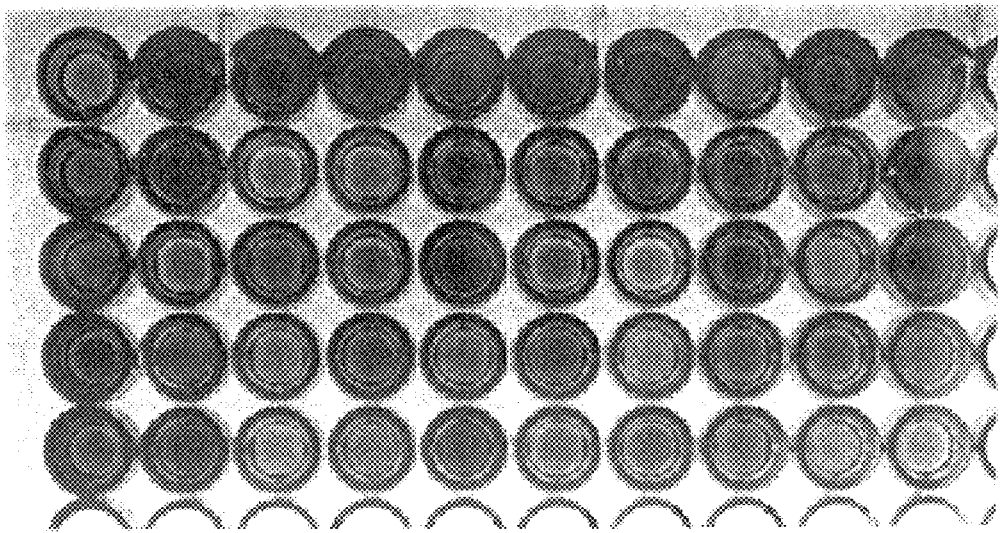
FIG. 3 is a photograph showing GUS activity staining of BY2 cell (50 samples) with INS(+)-p35Score-GUS introduced.
Figure 4:
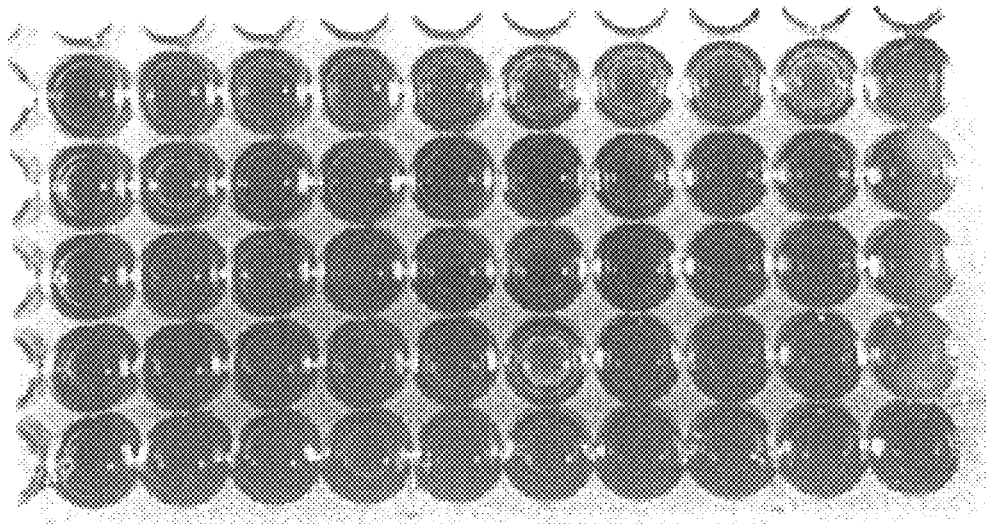
FIG. 4 is a photograph showing GUS activity staining of BY2 cell (50 samples) with INS-p35Score-GUS-INS introduced.
Figure 5:
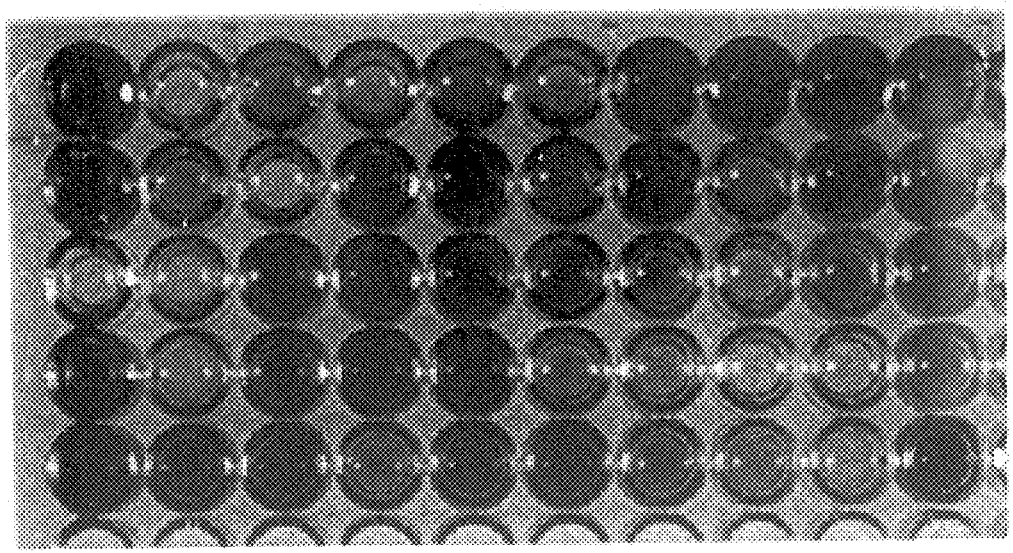
FIG. 5 is a photograph showing GUS activity staining of BY2 cell (50 samples) with p35Score-GUS-INS introduced.
Figure 6:
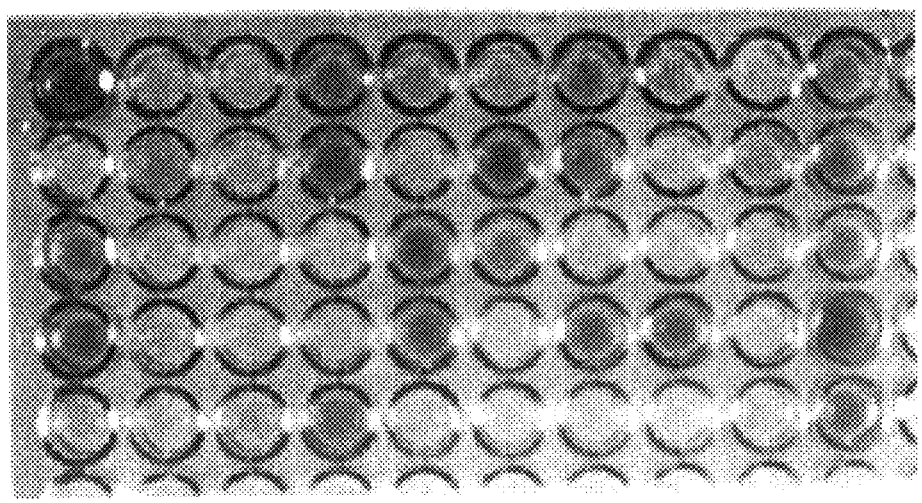
FIG. 6 is a photograph showing GUS activity staining of BY2 cell (50 samples) with 500-p35Score-GUS introduced.

In the p35Score-GUS (FIG. 1A) introduced cell, 42% of cells failed to exhibit GUS activity or exhibited only weak activity (+or −in Table 1, FIG. 2). Despite of it, in cells with INS(+)-p35Score-GUS (FIG. 1B) introduced, all of 50 clones were stained to blue color (+++ and ++ in Table 1, FIG. 3). In cells with INS-p35Score-GUS-INS (FIG. 1D) introduced, almost all clones were stained (FIG. 4), though one clone exhibited low GUS activity. On the contrary, the diversity of gene expression, observed in cells with p35Score-GUS-INS (FIG. 1E) introduced (FIG. 5), was the same as that observed in control cells. Negative control cells, with 500-p35Score-GUS (FIG. 1F) introduced, exhibited higher diversity in GUS activity (FIG. 6) compared with cells with p35Score-GUS (FIG. 1A) introduced. These results revealed that, expression stabilization of a transgene, introduced in chromosome of a plant cells, would be achieved by ligating sea urchin insulator to the transgene, either at one position of 5'-upstream of the transgene or two positions of both 5'-upstream and 3'-downstream of the transgene. It would be caused by inhibition of position effect, responsible for diversity of gene expression in a chromosome, achieved by introduction of the insulator.

Figure 7:
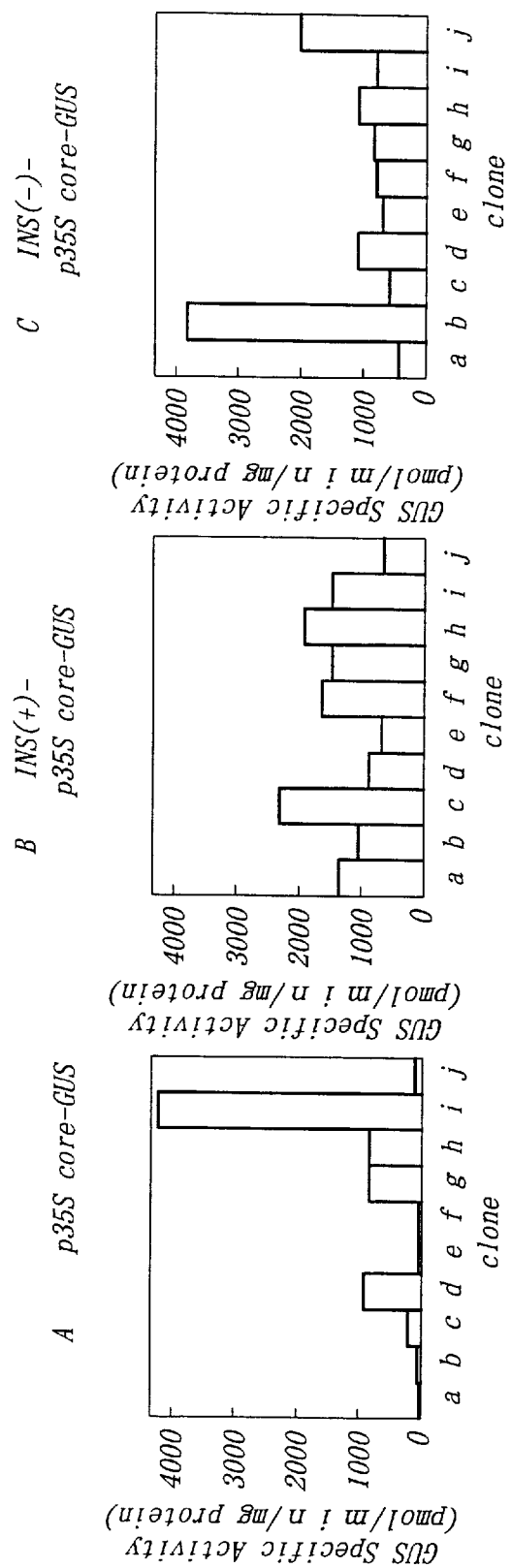
FIGS. 7A–7C are graphs showing results of GUS activity measured in BY2 cell with each plasmid constructed incorporated.

The enhancer suppressing effect observed in the presence of an insulator is direction-oriented. To investigate whether the effect caused by the Ars insulator is direction-oriented, INS(−)-p35Score-GUS (FIG. 1C) was introduced into BY2 cells. As the result, the diversity of GUS activity observed in cells with INS(+)-p35Score-GUS (FIG. 1B) introduced and that observed in cells with INS(−)-p35Score-GUS (FIG. 1C) introduced did not show significant difference (each 10 clones) (FIG. 7). Therefore, the insulator sequence exhibited stabilization of gene expression, independent of its direction. Moreover, the maximum value of GUS activity observed in cells with p35Score-GUS (FIG. 1A) introduced was higher than that observed in cells with INS(+)-p35Score-GUS (FIG. 1B) or INS(−)-p35Score-GUS (FIG. 1C) introduced (FIG. 7). These results indicate that the Ars insulator does not function as an enhancer that operates to enhance expression of downstream gene.

(Copy Numbers of Introduced Genes)

Figure 8:
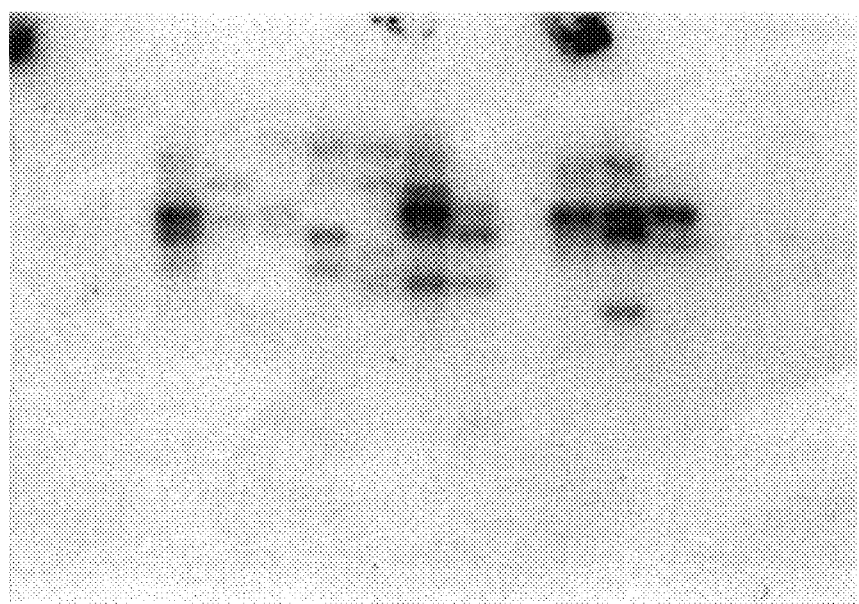
FIG. 8 is a photograph showing southern hybridization of BY2 cell with INS(+)-p35Score-GUS introduced, using DNA fragment of GUS gene as a probe.

Some examples using MAR reported achievement of stable expression of an exogenous gene caused by change of copy numbers of introduced genes. Moreover, some reports describes that gene expression is dependent to copy numbers. Therefore, southern hybridization was performed on 11 clones, with INS(+)-p35Score-GUS (FIG. 1B) introduced, using GUS gene as a probe. As the result, the copy number was estimated to be in the range of 1 to 5 and decrease of the copy number caused by addition of the insulator was not observed (FIG. 8). Moreover, the GUS activity corresponding to 1 copy was not constant and the extent of gene expression was not dependent of copy numbers. Further, T-DNA does not seem to be introduced into a certain (same) region of the chromosome by addition of the insulator.

In the practice of plant gene engineering technique, a plant body is used as a host. Therefore, introduction of a insulator into a plant body, not only cultured tobacco cell, was investigated. Then *Torenia fournieri*, which belongs to Scrophulariaceae, was adopted as a host plant used for introduction of the insulator. In this experiment, full length CaMV35S promoter was used as a promoter. Because the expression activity of the core CaMV35S promoter, which was used for introduction into BY2 cell, was too low in the torenia plant body. Therefore, a binary plasmid consisting of CaMV35S promoter ligated to GUS gene (CaMV35S-GUS gene) and an insulator derived from sea urchin arylsulfatase (Ars) was constructed. The plasmid was used to incorporate into Torenia.

Figure 9:
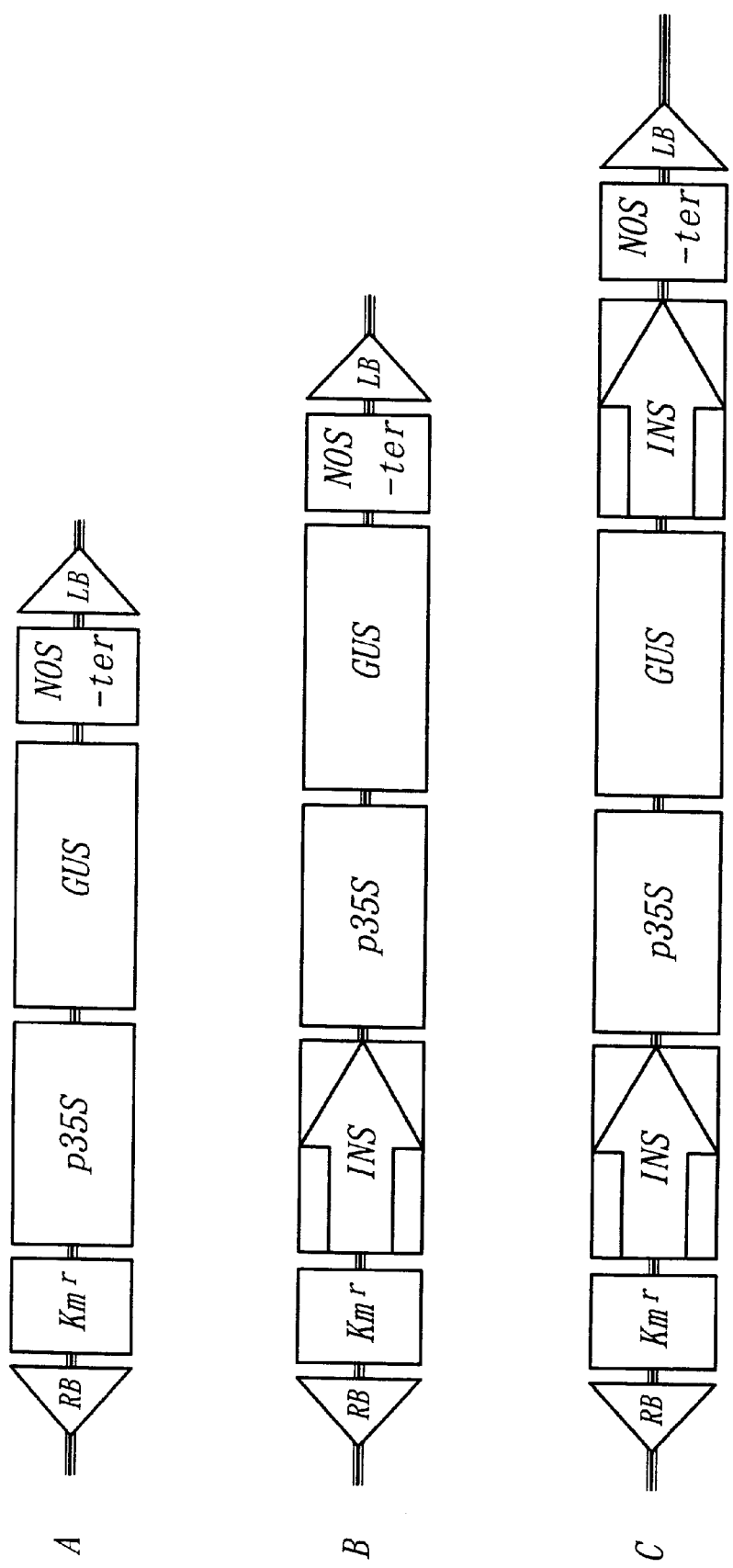
FIGS. 9A–9C are schematic views showing structure of T-DNA of binary plasmid introduced into Torenia.

Each plasmid constructed is shown in FIG. 9.

(A) CaMV35S-GUS as a control: construct A
(B) A fusion gene consisting of the insulator ligated to 5'-upstream of CaMV35S-GUS: construct B
(C) A fusion gene consisting of the insulators ligated to both 5'-upstream and 3'-downstream of CaMV35S-GUS: construct C (Introduction into Torenia Plant Body)

Three binary-plasmids described above were introduced into torenia using agrobacterium mediated method. The GUS activity of putative transformed plant bodies, which exhibited resistance against kanamycin according to lamina test, was measured using 4MUG as a substrate. The average value and the diversity of GUS activity were investigated on following samples.

(1) Nine plant bodies with construct A introduced.
(2) Eleven plant bodies with construct B introduced.
(3) Twelve plant bodies with construct C introduced.

The Torenia was grown under 16 hours of illumination at 25° C. and replanted each one month or two months. The leaves derived from Torenia plant bodies described above were used for the measurement of GUS activity. The GUS activity was measured twice, these are, about one month later and six months later from regeneration of the transgenic plant.

(GUS Activity Measurement of Transgenic Torenia Plant)

Increase of the GUS activity was observed in a transgenic plant with the fusion gene bearing the insulator introduced, compared with a transgenic plant with the control gene introduced. Though some diversity on the GUS activity among individual plant bodies was observed at both the first measurement and the second measurement. The average values of the 1st measurement, one month later from regeneration, are described below.

Construct A: 57(nmoles 4 MU/mg protein/30 min)
Construct B: 141(nmoles 4 MU/mg protein/30 min)
Construct C: 182(nmoles 4 MU/mg protein/30 min)

The results of the 2nd measurement, six months later from regeneration, were described below.

Construct A: 90(nmoles 4 MU/mg protein/30 min)
Construct B: 193(nmoles 4 MU/mg protein/30 min)
Construct C: 282(nmoles 4 MU/mg protein/30 min)

Figure 10:
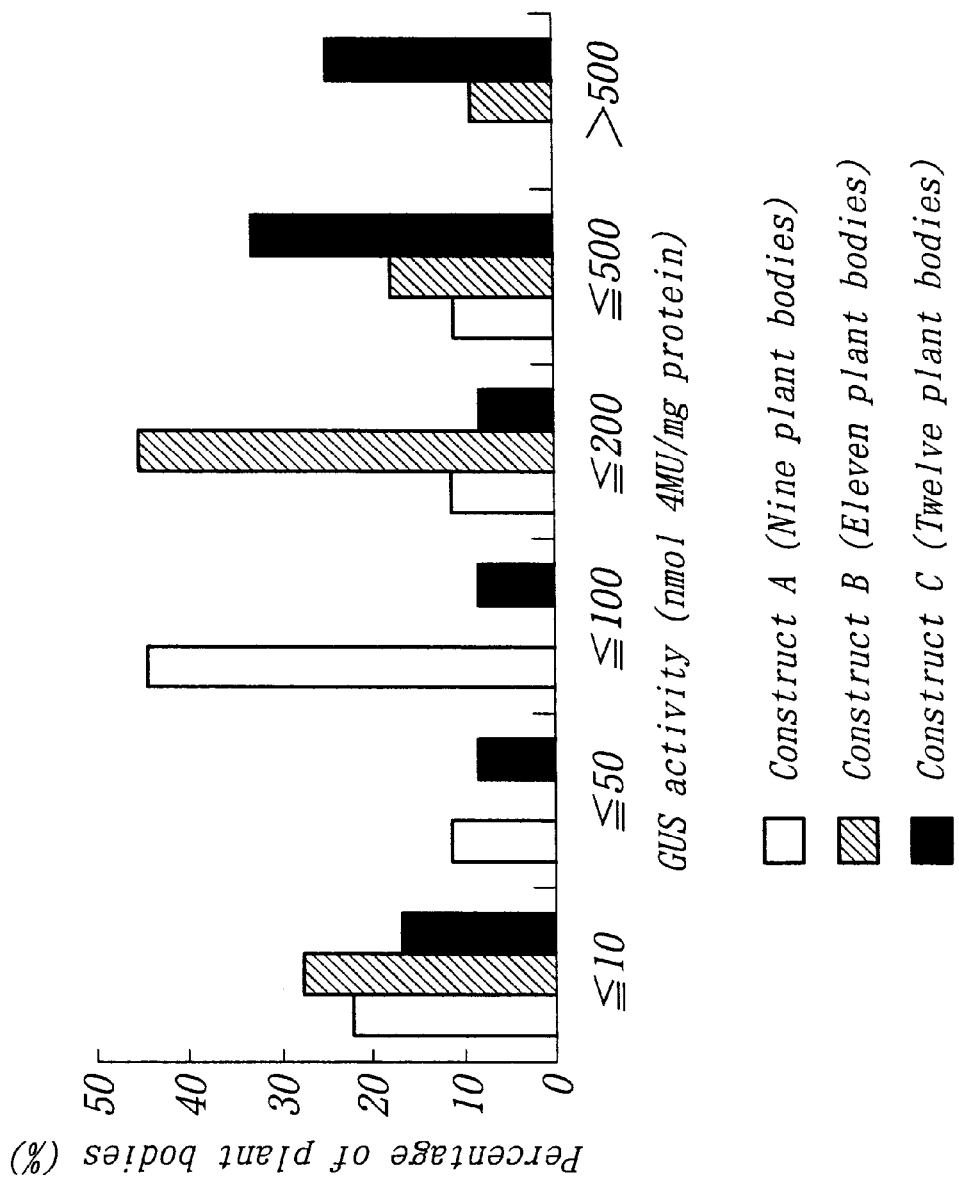
FIG. 10 is a graph showing distribution of GUS activity measured in transformed Torenia.

Moreover, distributions of the GUS activity observed at the 2nd measurement were shown in FIG. 10. The distributions of the GUS activity observed among plant bodies are described below, as ranges of the GUS activity observed in majority of plant bodies.

Construct A as a control: 50–100 (nmoles 4 MU/mg protein/30 min)
Construct B with the insulator ligated to 5'-upstream of CaMV35S-GUS: 100–200 (nmoles 4 MU/mg protein/30 min)
Construct C with the insulators ligated to both 5'-upstream and 3'-downstream of CaMV35S-GUS: 200–500 (nmoles 4 MU/mg protein/30 min)

In plant bodies with a fusion gene consisting of the insulator ligated to CaMV35S-GUS introduced, the number of plant bodies with no GUS activity or very weak GUS activity diminished significantly (FIG. 10). Therefore, an insulator derived from sea urchin would stabilize expression of an exogenous gene in a transformed torenia plant body.

An insulator would function to stabilize introduced gene in a plant cell. Therefore, stable expression of a transgene in a plant body would be achieved by this invention.

What is claimed is:

1. A method for introducing an exogenous gene into a plant, the method comprising introducing an exogenous gene operably linked to an insulator nucleotide sequence from the upstream sequence of a sea urchin arylsulfatase gene into the plant, so as to enable stable expression of said exogenous gene in said plant.

2. The method according to claim 1, wherein said insulator nucleotide sequence comprises the base sequence referred to as SEQ ID NO: 1 in the sequence list.

3. The method according to claim 1, wherein said plant is selected from the group consisting of tobacco, Arabidopsis, petunia, rice, maize, potato, sweet potato, soybean, strawberry, eggplant, blue gum and white poplar.

4. The method according to claim 1, wherein said exogenous gene is selected from the group consisting of peroxidase gene, chitinase gene, L-2,4-diaminobutyric acid acetyltransferase gene, L-2,4-diaminobutyric acid transaminase gene, and ectoine synthetase gene.

5. A transgenic plant which comprises an exogenous gene and an insulator nucleotide sequence from the upstream sequence of a sea urchin arylsulfatase gene, wherein said insulator enables stable expression of said exogenous gene in said plant.

6. The transgenic plant according to claim 5 belonging to the Scrophulariaceae.

7. The transgenic plant according to claim 5 which is *Torenia fournieri*.

8. The transgenic plant according to claim 5, wherein said insulator nucleotide sequence comprises SEQ ID NO: 1 in the sequence list.

9. The transgenic plant according to claim 5, wherein said plant is selected from the group consisting of tobacco, Arabidopsis, petunia, rice, maize, potato, sweet potato, soybean, strawberry, eggplant, blue gum and white poplar.

10. The transgenic plant according to claim 5, wherein said exogenous gene is selected from the group consisting of peroxidase gene, chitinase gene, L-2,4-diaminobutyric acid acetyltransgerase gene, L-2,4-diaminobutyric acid transaminase gene, ectoine synthetase gene, betaine synthetase gene, choline oxidase and fatty acid synthetase gene.

* * * * *

SEQUENCE LISTING

<160> NUMBER OF SEQ ID NOS: 1

<210> SEQ ID NO: 1
<211> LENGTH: 578
<212> TYPE: DNA
<213> ORGANISM: Sea urchin arylsulfatase

<400> SEQUENCE: 1

```
cccgggagca gaacccctgt aagctcaggg gtttttaggc gtttaattac ggtcagatga      60 gcaattttg ataccttaat ttgttgtgac actggtagtt aactattcat tctttcttgc     120
tctcttgctt tctatttctc tttaaaatgc ttttccaaaa gaatgggggg gggggggctgg    180 acgctcccga accccgacgt tccgcgggcc ctgacatgta agcatctcaa gaagcatatt    240
tcttgcctgg ctgttaattt acaaacgcat aaaaaaaata taatttacta aagaatgagg    300
aaaaatctcg ggaagttatg taatttcagc attatgtgta aaccaccgtt atggaataag    360
aaataaacca catttcaatt tatttccccc gagccccct ccccgatcaa tacgccagtg    420
ccccgccccg cccgcctccc gatctacact ttgttggcgg aaaaaatcgc aactgatctc    480
ccctaccttt cttctttctc tttcccttgc tctcctctta ccctttccct tccccaccct    540
tctccacaac ttgttggcgg gattacctgc aaattatc                            578
```